US011624064B2

(12) United States Patent
Cann et al.

(10) Patent No.: US 11,624,064 B2
(45) Date of Patent: Apr. 11, 2023

(54) ENRICHMENT OF MUTATED CELL FREE NUCLEIC ACIDS FOR CANCER DETECTION

(71) Applicant: GRAIL, LLC, Menlo Park, CA (US)

(72) Inventors: Gordon Cann, Redwood City, CA (US); Alex Aravanis, San Mateo, CA (US); Arash Jamshidi, Menlo Park, CA (US); Rick Klausner, Los Altos Hills, CA (US); Richard Rava, Redwood City, CA (US)

(73) Assignee: GRAIL, LLC, Menlo Park, CA (US)

( * ) Notice: Subject to any disclaimer, the term of this patent is extended or adjusted under 35 U.S.C. 154(b) by 1045 days.

(21) Appl. No.: 16/309,427

(22) PCT Filed: Jun. 13, 2017

(86) PCT No.: PCT/US2017/037223
§ 371 (c)(1),
(2) Date: Dec. 12, 2018

(87) PCT Pub. No.: WO2017/218512
PCT Pub. Date: Dec. 21, 2017

(65) Prior Publication Data
US 2019/0161752 A1    May 30, 2019

Related U.S. Application Data

(60) Provisional application No. 62/349,514, filed on Jun. 13, 2016, provisional application No. 62/357,812, filed on Jul. 1, 2016.

(51) Int. Cl.
| | |
|---|---|
| *C12N 15/10* | (2006.01) |
| *C12Q 1/6806* | (2018.01) |
| *C12Q 1/6827* | (2018.01) |
| *C12Q 1/6869* | (2018.01) |
| *C12Q 1/6809* | (2018.01) |
| *C12N 9/22* | (2006.01) |

(52) U.S. Cl.
CPC ........... *C12N 15/1093* (2013.01); *C12N 9/22* (2013.01); *C12Q 1/6806* (2013.01); *C12Q 1/6809* (2013.01); *C12Q 1/6827* (2013.01); *C12Q 1/6869* (2013.01); *C12N 2310/20* (2017.05); *C12N 2800/80* (2013.01)

(58) Field of Classification Search
None
See application file for complete search history.

(56) References Cited

U.S. PATENT DOCUMENTS

| | | | |
|---|---|---|---|
| 4,683,195 A | 7/1987 | Mullis et al. | |
| 6,818,395 B1 | 11/2004 | Quake et al. | |
| 7,169,560 B2 | 1/2007 | Lapidus et al. | |
| 7,282,337 B1 | 10/2007 | Harris et al. | |
| 7,666,593 B2 | 2/2010 | Lapidus | |
| 2002/0164629 A1 | 11/2002 | Quake et al. | |
| 2009/0026082 A1 | 1/2009 | Rothberg et al. | |
| 2009/0127589 A1 | 5/2009 | Rothberg et al. | |
| 2009/0156412 A1 | 6/2009 | Harris et al. | |
| 2009/0191565 A1 | 7/2009 | Lapidus et al. | |
| 2010/0035252 A1 | 2/2010 | Rothberg et al. | |
| 2010/0086533 A1 | 4/2010 | Montoya et al. | |
| 2010/0137143 A1 | 6/2010 | Rothberg et al. | |
| 2010/0188073 A1 | 7/2010 | Rothberg et al. | |
| 2010/0197507 A1 | 8/2010 | Rothberg et al. | |
| 2010/0282617 A1 | 11/2010 | Rothberg et al. | |
| 2010/0300559 A1 | 12/2010 | Schultz et al. | |
| 2010/0300895 A1 | 12/2010 | Nobile et al. | |
| 2010/0301398 A1 | 12/2010 | Rothberg et al. | |
| 2010/0304982 A1 | 12/2010 | Hinz et al. | |
| 2014/0356867 A1 | 12/2014 | Jon et al. | |
| 2016/0017396 A1* | 1/2016 | Cann et al. | C12N 15/102 506/26 |

FOREIGN PATENT DOCUMENTS

| | | |
|---|---|---|
| CN | 101679959 A | 3/2010 |
| EP | 2963113 A1 | 1/2016 |
| WO | 2000/070039 A1 | 11/2000 |
| WO | 2013/191775 A2 | 12/2013 |
| WO | 2015/075056 A1 | 5/2015 |
| WO | 2015/116686 A1 | 8/2015 |
| WO | 2016/014409 A1 | 1/2016 |
| WO | 2016/077350 A1 | 5/2016 |
| WO | 2016/186946 A1 | 11/2016 |
| WO | 2017/185086 A1 | 10/2017 |

OTHER PUBLICATIONS

Courtney et al., "CRISPR/Cas9 DNAcleavage at SNP-derived PAM enables both in vitro and in vivo KRT12 mutation-specific targeting," Gene Therapy 2016, 23:108-112, published online Aug. 20, 2015. (Year: 2015).*
Kleinstiver et al., "Engineered CRISPR-Cas9 nucleases with altered PAM specificities," Nature 2015, 523:481-485, published online Jun. 22, 2015. (Year: 2015).*
Bettegowda et al., "Detection of circulating tumor DNA in early- and late-stage human malignancies," (2014) SciTrans Med 6(224):1-11.
Braslavsky et al., "Sequence information can be obtained from single DNA molecules," (2003) PNAS, 100(7):3960-3964.
Carolin et al., "Structural Plasticity of PAM Recognition by Engineered Variants of the RNA-guided Endonuclease Cas9," (2016) Molecular Cell, 61(6):1097-2765.

(Continued)

*Primary Examiner* — Kaijiang Zhang

(74) *Attorney, Agent, or Firm* — Haynes and Boone, LLP

(57) ABSTRACT

Provided herein are methods of enriching mutated cell free nucleic acids for detection and diagnosis of cancer. Also provided are methods using a CRISPR-Cas system to target and deplete unwanted more abundant cell free nucleic acid sequences thereby enriching for less abundant sequences.

21 Claims, 12 Drawing Sheets

Specification includes a Sequence Listing.

(56) References Cited

OTHER PUBLICATIONS

Courtney, et al., "CRISPR/Cas9 DNA Cleavage at SNP-derived PAM Enables both In Vitro and In Vivo KRT12 Mutation-specific Targeting," (2015) Gene Therapy (23(1):108-112.
Duncavage, et al., "Hybrid Capture and Next-Generation Sequencing Identify Viral Integration Sites from Formalin-Fixed, Paraffin-Embedded Tissue," (2011) J Mol Diagn.13(3):5-333.
Harris et al., "Single-Molecule DNA Sequencing of a Viral Genome,",(2008) Science, 320:106-109.
Kleinstiver et al., "Broadening the Targeting Range of *Staphylococcus aureus* CRISPR-Cas9 by Modifying PAM Recognition," (2015) Nature Biotechnology 33(12):1293-1298.
Kleinstiver et al., "Engineered CRISPR-Cas9 Nuclease with Altered PAM Specificities," (2015) Nature, 523(7561):481-485.
Khurana et al., "Role of Non-coding Sequence Variants in Cancer," (2016) Nature Reviews, Genetics, 17(2):93-108.
Marguiles et al., "Genome sequencing in microfabricated high-density picolitre reactors," (2005) Nature 437(7057):376-380.
Maxam et al., "A new method for sequencing DNA," (1977) PNAS 74(2):560-564.
Moudrianakis et al., "Base Sequence Determination In Nucleic Acids With The Electron Microscope III. Chemistry and microscopy of guanine-labeled DNA," (1965) PNAS 53(3):564-671.
Mouliere et al., "Circulating tumor-derived DNA is shorter than somatic DNA in plasma," (2015) PNAS 112(11):3178-3179.
Mouliere et al., "Multi-marker Analysis of Circulating Cell-free DNA Toward Personalized Medicine for Colorectal Cancer," (2014) Mol Oncol. 8(5):927-947.
Newman et al., "An ultrasensitive method for quantitating circulating tumor DNA with broad patient coverage,"(2014) Nat Med 20(5):548-554.
Sanger, et al., "DNA sequencing with chain-terminating inhibitors," (1977) PNAS 74(12):5463-5467.
Soni et al., "Progress toward ultrafast DNA sequencing using solid-state nanopores," (2007) Clin. Chem. 53(11):1996-2001.
Shin et al., "Permanent Inactivation of Huntington's Disease Mutation by Personalized Allele-specific CRISPR/Cas9," (2016) Human Molecular Genetics, p. ddw286.
Tseng et al., "Dynamic Plasma EGFR Mutation Status as a Predictor of EGFR-TKI Efficacy in Patients with EGFR-Mutant Lung Adenocarcinoma, " (2015) J Thorac Oncol 10(4):603-610.

* cited by examiner

700

| | GeneName | REF | ALT | Mutation | Strategy |
|---|---|---|---|---|---|
| | AKT1 | C | T | E17K | Cas9 PAM mutant |
| A | BRAF | A | T | V600E | Single base specificity |
| | BRAF | G | C | L597V | Single base specificity |
| | BRAF | C | G | G469A | Cas9 PAM mutant |
| | BRAF | C | A | G466V | Cas9 PAM mutant |
| | EGFR | AAAC | A | E709_T710delins | Multiple base specificity |
| | EGFR | G | A | G719S | Cas9 PAM mutant |
| | EGFR | G | T | G719C | Cas9 PAM mutant |
| | EGFR | G | C | G719A | Cas9 PAM mutant |
| B | EGFR | AGGAATTAAGAGAAGC | A | Exon19del | PAM in wt, not in deletion |
| | EGFR | AGGAATTAAGAGAAGC | A | Exon19del | PAM in wt, not in deletion |
| | EGFR | C | T | T790M | Single base specificity |
| | EGFR | T | G | L858R | Cpf1 PAM mutated |
| | EGFR | T | A | L861Q | Cpf1 PAM mutated |

| GeneName | REF | ALT | Mutation | Strategy |
|---|---|---|---|---|
| KRAS | T | A | Q61H | Single base specificity |
| KRAS | T | G | Q61H | Single base specificity |
| KRAS | T | A | Q61L | Single base specificity |
| KRAS | T | C | Q61R | Single base specificity |
| KRAS | G | T | Q61K | Single base specificity |
| KRAS | C | G | G13A | Cas9 PAM mutant |
| KRAS | C | T | G13D | Cas9 PAM mutant |
| KRAS | C | A | G13C | Cas9 PAM mutant |
| KRAS | C | G | G13R | Cas9 PAM mutant |
| KRAS | C | T | G13S | Cas9 PAM mutant |
| KRAS | C | A | G12V | Cas9 PAM mutant |
| KRAS | C | G | G12A | Cas9 PAM mutant |
| KRAS | C | T | G12D | Cas9 PAM mutant |
| KRAS | C | A | G12C | Cas9 PAM mutant |
| KRAS | C | G | G12R | Cas9 PAM mutant |
| KRAS | C | T | G12S | Cas9 PAM mutant |

C ← (indicating G12D row)

| GeneName | REF | ALT | Mutation | Strategy |
|---|---|---|---|---|
| MAP2K1 | A | C | Q56P | Single base specificity |
| NRAS | T | G | Q61H | Single base specificity |
| NRAS | T | A | Q61L | Single base specificity |
| NRAS | T | C | Q61R | Single base specificity |
| NRAS | G | T | Q61K | Single base specificity |
| NRAS | C | G | G12A | Cas9 PAM mutant |
| NRAS | C | T | G12D | Cas9 PAM mutant |
| NRAS | C | A | G12C | Cas9 PAM mutant |
| NRAS | C | G | G12R | Cas9 PAM mutant |
| NRAS | C | T | G12S | Cas9 PAM mutant |
| PIK3CA | G | A | E542K | Single base specificity |
| PIK3CA | G | C | E545Q | Single base specificity |
| PIK3CA | G | A | E545K | Single base specificity |
| PIK3CA | A | G | H1047R | Single base specificity |
| PIK3CA | A | T | H1047L | Single base specificity |
| PTEN | C | T | R233* | Single base specificity |

FIG. 7, continued

SEQUENCE LISTING

<160> NUMBER OF SEQ ID NOS: 1

<210> SEQ ID NO 1
<211> LENGTH: 16
<212> TYPE: DNA
<213> ORGANISM: Unknown
<220> FEATURE:
<221> NAME/KEY: source
<223> OTHER INFORMATION: /note="Description of Unknown:
      Mutated EGFR oligonucleotide"

<400> SEQUENCE: 1
aggaattaag agaagc                                                    16

ENRICHMENT OF MUTATED CELL FREE NUCLEIC ACIDS FOR CANCER DETECTION

CROSS REFERENCE TO RELATED APPLICATIONS

This application is a national stage entry application filed under 35 USC § 371 of PCT Application No. PCT/US2017/037223, filed Jun. 13, 2017, which claims priority benefit of the filing date of U.S. Provisional Patent Application No. 62/349,514, filed on Jun. 13, 2016 and also claims priority benefit of the filing date of U.S. Provisional Patent Application No. 62/357,812, filed on Jul. 1, 2016, the disclosures of which applications are herein incorporated by reference in their entireties.

SEQUENCE LISTING

The instant application contains a Sequence Listing which has been submitted electronically in ASCII format and is hereby incorporated by reference in its entirety. Said ASCII copy, created on Jun. 28, 2017, is named GRA-0021-WO_SL.txt and is 580 bytes in size.

INTRODUCTION

Provided herein are methods of enriching mutated cell free nucleic acids for detection and diagnosis of cancer. Also provided are methods of using a CRISPR-Cas system to target and deplete unwanted, more abundant cell free nucleic acid sequences, thereby enriching for less abundant sequences.

BACKGROUND

Analysis of circulating cell free nucleic acids (e.g., cell free DNA (cfDNA) and/or cell free RNA (cfRNA)) using next generation sequencing (NGS) is recognized as a valuable diagnostic tool for detection and diagnosis of cancer. However, in a complex sample, such as a plasma sample, sequences from a wild-type allele, for example, can overwhelm detection of a mutant allele during NGS analysis of cfDNA. In another example, transcripts from highly expressed genes can overwhelm detection of less abundant transcripts during NGS analysis of an RNA-Seq library prepared from cfRNA. There is a need for new methods for depleting unwanted more abundant cell free nucleic acid sequences and enriching mutated nucleic acid sequences from a population of cell free nucleic acids for detection and diagnosis of cancer.

SUMMARY

Aspects of the invention include methods for enriching a plurality of target nucleic acids in a sample, the methods comprising providing an endonuclease system, wherein each of the plurality of target nucleic acids comprises a first variant and a second variant, wherein the endonuclease system comprises a plurality of clustered regularly interspaced short palindromic repeat (CRISPR) RNAs (crRNAs), or derivatives thereof, each crRNA comprising a targeting sequence, and a plurality of CRISPR-associated (Cas) proteins, or variants thereof, each Cas protein capable of binding to a protospacer adjacent motif (PAM) site on a target nucleic acid, wherein the first variant of each target nucleic acid comprises a PAM site adjacent to a region complementary to a crRNA targeting sequence, and wherein the second variant does not comprise the PAM site or does not comprise the region complementary to the crRNA targeting sequence adjacent to the PAM site, and contacting the sample with the endonuclease system, thereby depleting the first variant and enriching the second variant of each of the plurality of target nucleic acids in the sample.

In some embodiments, the first variant of each target nucleic acid comprises a PAM site adjacent to a region complementary to a crRNA targeting sequence, and the second variant does not comprise the PAM site. In some embodiments, the first variant of each target nucleic acid comprises a PAM site adjacent to a region complementary to a crRNA targeting sequence, and the second variant does not comprise the region complementary to the crRNA targeting sequence adjacent to the PAM site. In some embodiments, the first variant of each target nucleic acid comprises a PAM site adjacent to a region complementary to a crRNA targeting sequence, and the second variant does not comprise the region complementary to the crRNA targeting sequence. In some embodiments, the methods comprise amplifying the enriched second variants of the plurality of target nucleic acids to produce an enriched sequencing library. In some embodiments, the methods comprise sequencing the enriched sequencing library to detect structural rearrangements or mutations in the target nucleic acids in the sample.

In some embodiments, the first variant of each of the plurality of target nucleic acids is depleted by more than 50%, more than 60%, more than 70%, more than 80%, more than 90%, more than 95%, more than 98%, more than 99%, more than 99.9%, more than 99.99%, or more than 99.999% after contacting the sample with the endonuclease system, relative to the first variant level in the sample prior to contacting the sample with the endonuclease system. In some embodiments, the plurality of target nucleic acids is between 2 and 100, between 2 and 80, between 2 and 60, between 2 and 40, between 2 and 20, between 2 and 10 target nucleic acids. In some embodiments, the plurality of target nucleic acids is between 2 and 100, between 10 and 100, between 20 and 100, between 30 and 100, between 40 and 100, between 50 and 100, between 60 and 100, between 70 and 100, between 80 and 100, or between 90 and 100 target nucleic acids.

In some embodiments, the first variant of each of the plurality of target nucleic acids is more abundant in the sample than the second variant. In some embodiments, the first variant of each of the plurality of target nucleic acids in the sample comprises at least 60%, at least 70%, at least 80%, at least 90%, at least 95%, at least 98%, at least 99%, at least 99%, at least 99.9%, at least 99.99%, or at least 99.999% of each of the target nucleic acids in the sample. In some embodiments, the first variant of each of the plurality of target nucleic acids comprises a wild-type allele sequence. In some embodiments, the wild-type allele sequence comprises a AKT1, BRAF, EGFR, KRAS, MAP2K1, NRAS, PI3KCA or PTEN wild-type allele sequence.

In some embodiments, the second variant of each of the plurality of target nucleic acids comprise a mutant allele sequence. In some embodiments, the mutant allele sequence comprises a AKT1, BRAF, EGFR, KRAS, MAP2K1, NRAS, PI3KCA or PTEN mutant allele sequence. In some embodiments, the mutant allele sequence comprises a AKT1-E17K, BRAF-V600E, BRAF-L597V, BRAF-G469A, BRAF-G466V, EGFR-E709 T710delins, EGFR-G719S, EGFR-G719C, EGFR-G719A, EGFR-Exon19del, EGFR-T790M, EGFR-L858R, EGFR-L861Q, KRAS- Q61H, KRAS-Q61L, KRAS-Q61R, KRAS-Q61K, KRAS-G13A, KRAS-G13D, KRAS-G13C, KRAS-G13R, KRAS-G13D, KRAS-G13C, KRAS-G13R, KRAS-G13S, KRAS-G12V, KRAS-G12A, KRAS-G12D, KRAS-G12D, KRAS-G12C, KRAS-G12R, KRAS-G12S, MAP2K1-Q56P, NRAS-Q61H, NRAS-Q61L, NRAS-Q61R, NRAS-Q61K, NRAS-G12A, NRAS-G12D, NRAS-G12C, NRAS-G12R, NRAS-G12S, PI3KCA-E542K, PI3KCA-E545Q, PI3KCA-E545K, PI3KCA-H1047R, PI3KCA-H1047L, or PTEN-R233* mutant allele sequence.

In some embodiments, the mutant allele sequence comprises a mutant allele sequence according to FIG. 7. In some embodiments, the sample is a blood, serum, plasma, urine, or cerebrospinal fluid sample. In some embodiments, the sample was obtained from a human cancer patient. In some embodiments, the plurality of target nucleic acids comprise cell-free DNA (cfDNA) or cell-free RNA (cfRNA). In some embodiments, the plurality of Cas proteins comprises Cas9, or a variant thereof, a Cas9 ortholog, or a variant thereof, or Cpfl, or a variant thereof. In some embodiments, the Cas9, or variant thereof, is derived from *Streptococcus pyogenes*, or wherein the Cpfl, or variant thereof, is derived from *Francisell novicida* U112. In some embodiments, each of the plurality of Cas proteins comprises two active nuclease domains. In some embodiments, each of the plurality of target nucleic acids are double stranded nucleic acids. In some embodiments, the endonuclease system produces a blunt-ended double-strand break in one or more target nucleic acids. In some embodiments, the endonuclease system produces a staggered double-strand break in one or more target nucleic acids.

In some embodiments, the first variant of one or more of the plurality of target nucleic acid sequences comprises a PAM site comprising the sequence 5'-NGG-3', wherein N comprises A, G, C, or T, and wherein the second variant does not comprise the PAM site. In some embodiments, the first variant of one or more of the plurality of target nucleic acid sequences comprises a PAM site comprising the sequence 5'-TTN-3', wherein N comprises A, G, C, or T, and wherein the second variant does not comprise the PAM site. In some embodiments, the first variant of one or more of the plurality of target nucleic acid sequences comprises a PAM site, and wherein the second variant comprises a deletion of the PAM site. In some embodiments, the first variant of one or more of the plurality of target nucleic acid sequences comprises a region complementary to a crRNA targeting sequence adjacent to a PAM site and the second variant comprises an insertion of 1 or more, 2 or more, 3 or more, 4 or more, 5 or more, 6 or more, 7 or more, 8 or more, 9 or more, 10 or more, 12 or more, 14 or more, 16 or more, 18 or more, or 20 or more base pairs (bps) within 50 bps, 40 bps, 30 bps, 20 bps, or 10 bps upstream of the PAM site.

In some embodiments, the first variant of one or more of the plurality of target nucleic acid sequences comprises a region complementary to a crRNA targeting sequence adjacent to a PAM site, and the second variant does not comprise the region complementary to the crRNA targeting sequence adjacent to the PAM site. In some embodiments, in the second variant the region adjacent to the PAM site comprises a point mutation. In some embodiments, in the second variant the region adjacent to the PAM site comprises the junction of a fusion gene. In some embodiments, the endonuclease system further comprises a crRNA and Cas protein targeting an abundant wild-type target nucleic acid in the sample. In some embodiments, the abundant wild-type target nucleic acid is selected from the group consisting of a ribosomal RNA and a globin RNA.

Aspects of the invention include methods for analyzing the genome of a cancer patient, the methods comprising providing an endonuclease system, wherein the endonuclease system comprises a plurality of crRNAs, or derivatives thereof, each crRNA comprising a targeting sequence, and a plurality of Cas proteins, or variants thereof, each Cas protein capable of binding to a PAM site on a target nucleic acid; contacting a sample obtained from the cancer patient comprising a plurality of target nucleic acids with the endonuclease system to obtain a pool of target nucleic acid fragments; sequencing the pool of target nucleic acid fragments to obtain sequencing data from the cancer patient, and comparing the sequencing data from the cancer patient with sequencing data from a reference genome fragmented by the endonuclease system to detect structural rearrangements and mutations in the genome of the cancer patient.

In some embodiments, the sequencing data comprises comparing the fragmentation pattern of the pool of target nucleic acids from the cancer patient with the fragmentation pattern of a pool of target nucleic acids in the reference genome.

In some embodiments, the method comprises contacting a sample obtained from a healthy subject comprising a plurality of target nucleic acids with the endonuclease system to obtain a pool of target nucleic acid fragments, and sequencing the pool of target nucleic acid fragments to obtain the sequencing data from the reference genome. In some embodiments, the endonuclease system cleaves target nucleic acids in a sample from a healthy subject at a predetermined interval. In some embodiments, the predetermined interval is about 300 bp.

BRIEF DESCRIPTION OF THE DRAWINGS

FIG. 7 shows a table of an example of a screening strategy for hotspot mutations in non-small cell lung cancer (NSCLC).

DETAILED DESCRIPTION

Figure 1:
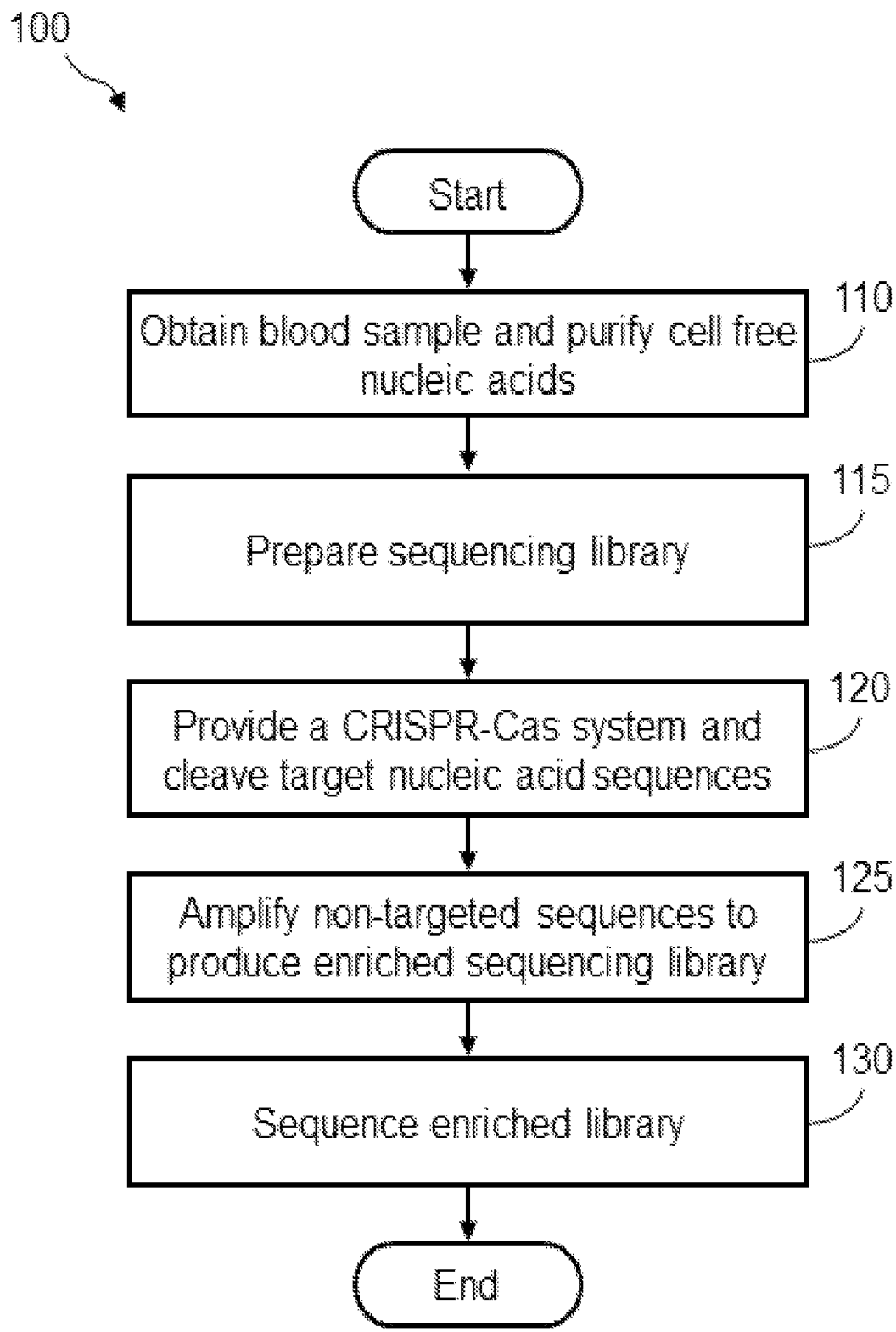
FIG. 1 illustrates a flow diagram of an example of a method of enriching mutated nucleic acids in a NGS library prepared from cell free nucleic acids isolated from a biological sample (e.g., human plasma, urine or cerebral spinal fluid samples).

Provided herein are methods of enriching mutated cell free nucleic acids for detection and diagnosis of cancer. In various embodiments, the methods provided herein use a CRISPR-Cas system to target and deplete unwanted more abundant cell free nucleic acid sequences, thereby enriching for less abundant sequences.

Class 2 CRISPR-Cas systems generally includes a CRISPR ("clustered regularly interspaced short palindromic repeat") RNA (crRNA) and a CRISPR-associated (Cas) protein, wherein the crRNA is a guide RNA that contains a target-specific nucleotide sequence ("targeting sequence") complementary to a region of a target nucleic acid. The targeting sequence of a guide RNA can be designed to target any DNA sequence that is adjacent to a PAM (protospacer adjacent motif) site. Cas protein binding at a target site is initiated by recognition of the PAM site that is adjacent to a targeted DNA sequence. Subsequent cleavage of the targeted site occurs if the guide RNA targeting sequence successfully hybridizes to the target sequence.

In some embodiments, the methods provided herein are used to enhance the detection of mutant alleles in a next generation sequencing (NGS) library prepared from cell free DNA (cfDNA) isolated from a biological sample (e.g., a plasma sample). In one example, the cfDNA includes circulating tumor DNA (ctDNA) that includes a mutation (e.g., a single nucleotide mutation, an insertion, or a deletion).

In some embodiments, the methods provided herein are used to enhance the detection of less abundant mutant transcripts in an RNA sequencing (RNA-Seq) library prepared from cell free RNA (cfRNA) isolated from a biological sample (e.g., a plasma sample). In some embodiments, the methods provided herein are used for enriching RNA fusions in cell free nucleic acids isolated from a biological sample, (e.g., a plasma sample).

In some embodiments, a CRISPR-Cas system includes a Cas9 protein or variant thereof. Cas9 is guided to a target nucleic acid site by a crRNA that includes a targeting sequence of about 20 bases, and a trans-activating crRNA (tracrRNA). In some embodiments, the Cas9 crRNA and the tracrRNA are fused to form a hybrid single guide RNA (sgRNA). Binding of a target site by Cas9 is initiated by recognition of a PAM site 3' to the target DNA site. Cas9 then produces a blunt-end double-stranded break in the target DNA if the guide RNAs (e.g., sgRNA) successfully hybridizes with the adjacent target sequence.

In some embodiments, a CRISPR-Cas system includes a Cpf1 protein or variant thereof. Cpf1 is guided to a target nucleic acid region by a single CRISPR guide RNA that includes a targeting sequence of about 24 bases. Binding of a target site by Cpf1 is initiated by recognition of a PAM site 5' to the target DNA site. Cpf1 then produces a staggered double-stranded break in the target DNA if the guide RNAs (e.g., sgRNA) successfully hybridizes with the adjacent target sequence.

In some embodiments, provided herein is a "tool box" of Cas proteins (e.g., Cas9 or variants thereof, Cas9 orthologs or variants thereof, Cpf1 or variants thereof) that are programmed with a set of guide RNAs having different target specificities. The tool box (or pool or library) of Cas proteins programmed with a set of guide RNAs having different target specificities constitutes an "enzymatic enrichment panel" that can be used for multiplexed enrichment of multiple target sequences. In one example, the pool of Cas proteins can be programmed with a set of guide RNAs designed to target abundant library fragments representative of rRNA allowing enrichment of lower abundance transcripts during whole transcriptome analysis. The tool box can include, for example, (1) Cas9 proteins programmed to target a set of wild-type alleles that include a specific PAM site; (2) Cas9 ortholog(s) programmed to target a set of wild-type alleles that include different PAM sites; (3) Cas9 proteins (or orthologs) programmed with guide RNAs having targeting sequences with enhanced specificity for wild-type alleles; and (4) variants of Cas9 proteins or orthologs with enhanced ability to target single base mutations.

CRISPR-Cas Mediated Enrichment of Mutated Cell Free Nucleic Acids

In one aspect, provided herein are methods for enriching a plurality of target nucleic acids in a sample, comprising providing an endonuclease system, wherein each of the plurality of target nucleic acids comprises a first variant and a second variant, wherein the endonuclease system comprises a plurality of clustered regularly interspaced short palindromic repeat (CRISPR) RNAs (crRNAs), or derivatives thereof, each crRNA comprising a targeting sequence, and a plurality of CRISPR-associated (Cas) proteins, or variants thereof, each Cas protein capable of binding to a protospacer adjacent motif (PAM) site on a target nucleic acid, wherein the first variant of each target nucleic acid comprises a PAM site adjacent to a region complementary to a crRNA targeting sequence, and wherein the second variant does not comprise the PAM site or does not comprise the region complementary to the crRNA targeting sequence adjacent to the PAM site, and contacting the sample with the endonuclease system, thereby depleting the first variant and enriching the second variant of each of the plurality of target nucleic acids in the sample.

In some embodiments, the methods comprise amplifying the enriched second variants of the plurality of target nucleic acids to produce an enriched sequencing library. In some embodiments, the methods comprise sequencing the enriched sequencing library to detect structural rearrangements or mutations in the target nucleic acids in the sample. In some embodiments, the methods comprise sequencing the enriched sequencing library to detect structural rearrangements or mutations in the target nucleic acids in the sample.

In some embodiments, the first variant of each of the plurality of target nucleic acids is depleted by more than 50%, more than 60%, more than 70%, more than 80%, more than 90%, more than 95%, more than 98%, more than 99%, more than 99.9%, more than 99.99%, or more than 99.999% after contacting the sample with the endonuclease system, relative to the first variant level in the sample prior to contacting the sample with the endonuclease system.

In some embodiments, the first variant of each of the plurality of target nucleic acids is depleted by more than 50%, more than 60%, more than 70%, more than 80%, more than 90%, more than 95%, more than 98%, more than 99%, more than 99.9%, more than 99.99%, or more than 99.999% after contacting the sample with the endonuclease system, relative to the first variant level in the sample prior to contacting the sample with the endonuclease system. In some embodiments, the plurality of target nucleic acids is between 2 and 100, between 2 and 80, between 2 and 60, between 2 and 40, between 2 and 20, between 2 and 10 target nucleic acids. In some embodiments, the plurality of target nucleic acids is between 2 and 100, between 10 and 100, between 20 and 100, between 30 and 100, between 40 and 100, between 50 and 100, between 60 and 100, between 70 and 100, between 80 and 100, or between 90 and 100 target nucleic acids.

In some embodiments, the first variant of each of the plurality of target nucleic acids is more abundant in the sample than the second variant. In some embodiments, the first variant of each of the plurality of target nucleic acids in the sample comprises at least 60%, at least 70%, at least 80%, at least 90%, at least 95%, at least 98%, at least 99%, at least 99%, at least 99.9%, at least 99.99%, or at least 99.999% of each of the target nucleic acids in the sample.

In some embodiments, the plurality of Cas proteins comprises Cas9, or a variant thereof, a Cas9 ortholog, or a variant thereof, or Cpf1, or a variant thereof. In some embodiments, the Cas9, or variant thereof, is derived from *Streptococcus pyogenes*, or wherein the Cpf1, or variant thereof, is derived from *Francisell novicida* U112. In some embodiments, each of the plurality of Cas proteins comprises two active nuclease domains. In some embodiments, each of the plurality of target nucleic acids are double stranded nucleic acids. In some embodiments, the endonuclease system produces a blunt-ended double-strand break in one or more target nucleic acids. In some embodiments, the endonuclease system produces a staggered double-strand break in one or more target nucleic acids.

In some embodiments, the sample is a blood, serum, plasma, urine, or cerebrospinal fluid sample. In some embodiments, the sample was obtained from a human cancer patient. In some embodiments, the plurality of target nucleic acids comprise cell-free DNA (cfDNA) or cell-free RNA (cfRNA).

FIG. 1 illustrates a flow diagram of an example of a method 100 of enriching mutated nucleic acids in a NGS library prepared from cell free nucleic acids isolated from a biological sample (e.g., a plasma sample).

In a step 110, a blood sample is obtained and circulating cell-free nucleic acids are isolated from the plasma fraction.

In a step 115, a sequencing library is prepared. In one example, the sequencing library is an NGS library prepared from cell free DNA. In another example, the sequencing library is an RNA-Seq library prepared from cell free RNA.

In a step 120, a CRISPR-Cas system is provided and targeted nucleic acid sequences are cleaved. The CRISPR-Cas system binds to the targeted sequence(s) and cleaves it. Because the system creates a double stranded break in the targeted sequence(s), these sequences cannot serve as templates for subsequent amplification reactions. Examples of targeted depletion of unwanted sequences for enrichment of mutated sequences are described in more detail with reference to FIGS. 2A and 2B, FIGS. 3A and 3B, FIGS. 4A and 4B, FIGS. 5A and 5B, and FIGS. 6A and 6B.

In a step 125, non-targeted sequences are amplified to produce an enriched sequencing library.

In a step 130, the enriched library is sequenced. In one example, sequencing is performed using a MiSeq, NextSeq or HiSeq system (Illumina, Inc.).

Depletion of Wild-Type Allele for Detection of Mutant Allele

Wild-type DNA sequences can overwhelm detection of mutant DNA during analysis of cell free nucleic acids (e.g., ctDNA) from a biological sample. Provided herein are methods of enriching a mutant DNA sequence in a population of wild-type DNA sequences, wherein the wild-type allele of a target nucleic acid is depleted using differential CRISPR-Cas binding and cleavage. Cas protein binding at a target site is initiated by recognition of a PAM site that is adjacent to a targeted DNA sequence. Subsequent cleavage of the targeted site occurs if there is complete or near complete homology between the crRNA target sequence and the targeted DNA sequence. Mutations that ablate a PAM site prevent Cas protein binding and subsequent cleavage of the mutant DNA sequence.

In some embodiments, the wild-type allele sequence comprises a AKT1, BRAF, EGFR, KRAS, MAP2K1, NRAS, PI3KCA or PTEN wild-type allele sequence.

In some embodiments, the second variant of each of the plurality of target nucleic acids comprise a mutant allele sequence.

In some embodiments, the mutant allele sequence comprises a AKT1, BRAF, EGFR, KRAS, MAP2K1, NRAS, PI3KCA or PTEN mutant allele sequence.

PAM Site Recognition for Differential Cleavage and Enrichment of Mutations in ctDNA In some embodiments, the first variant of each target nucleic acid comprises a PAM site adjacent to a region complementary to a crRNA targeting sequence, and the second variant does not comprise the PAM site.

In some embodiments, the region in the second variant corresponding to the PAM site in the first variant comprises a point mutation (e.g., 1 bp, 2 bps, or 3 bps point mutation). In some embodiments, the region in the second variant corresponding to the PAM site comprises a deletion mutation (e.g., deletion of 1 bp, 2 bps, 3 bps, 4 bps, 5 bps, 6 bps, 7 bps, 8 bps, 9 bps, 10 bps, or more).

In some embodiments, the target nucleic acid comprising a mutation in a PAM site comprises AKT1 (e.g., AKT-E17K), BRAF (e.g., BRAF-G469A, BRAF-G466V), EGFR (e.g., EGFR-G719S, EGFR-G719C, EGFR-G719A, EGFR-L858R, EGFR-L861Q), KRAS (e.g., KRAS-G13A, KRAS-G13D, KRAS-G13C, KRAS-G13R, KRAS-G13S, KRAS-G12V, KRAS-G12A, KRAS-G12D, KRAS-G12C, KRAS-G12R, KRAS-G12S), NRAS (e.g., NRAS-G12A, NRAS-G12D, NRAS-G12C, NRAS-G12R, NRAS-G12S).

In some embodiments, the mutation in the PAM site (e.g., mutation in a region in the second variant corresponding to the PAM site of the first variant) comprises a C>A, C>G, C>T, G>A, G>C, G>T, T>A, or T>G mutation.

In some embodiments, the target nucleic acid comprising a mutation in a PAM site comprises a target gene or mutation as shown in FIG. 7.

In some embodiments, the first variant of one or more of the plurality of target nucleic acid sequences comprises a PAM site comprising the sequence 5'-NGG-3', wherein N comprises A, G, C, or T, and wherein the second variant does not comprise the PAM site.

Figure 2A:
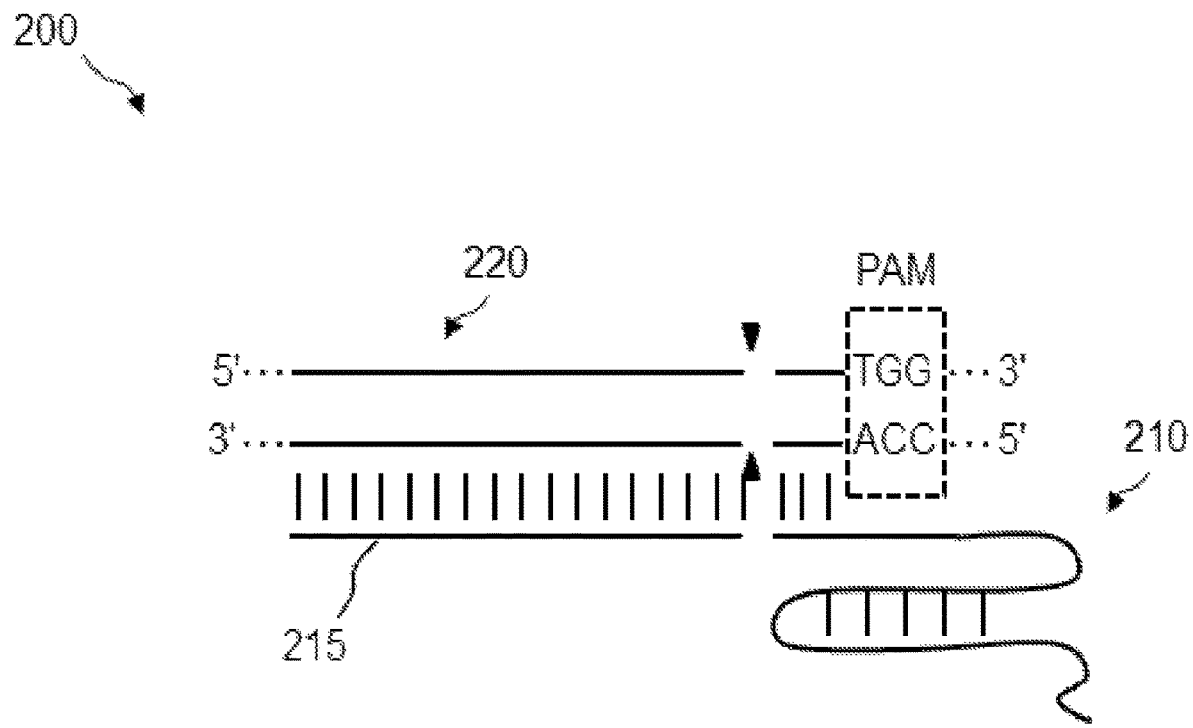
FIGS. 2A and 2B illustrate an example of a process of using Cas9 to selectively deplete a wild-type allele and enrich a mutant allele.
Figure 2B:
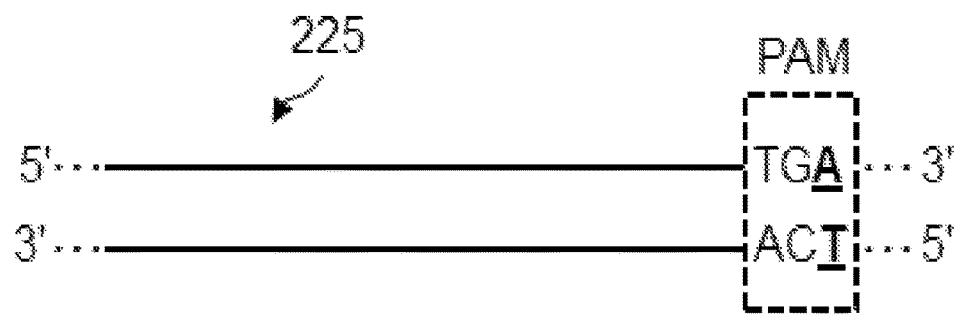

FIGS. 2A and 2B illustrate an example of a process 200 of using Cas9 to selectively deplete a wild-type allele and enrich a mutant allele. The PAM sequence for Cas9 derived from *Streptococcus pyogenes* is 5'-NGG-3'. In this example, the sequence 5'-TGG-3' is the PAM sequence in a wild-type KRAS allele. Referring to FIG. 2A, a guide RNA 210 (e.g., sgRNA) that includes a 20 base targeting sequence 215 is used in conjunction with Cas9 (not shown) to target a wild-type KRAS sequence 220. Targeting sequence 215 is complementary to wild-type KRAS sequence 220. Binding of Cas9 (not shown) to the PAM sequence initiates interrogation of the targeted sequences 5' to the PAM site and hybridization of targeting sequence 215 to complementary sequence in wild-type KRAS sequence 220. Hybridization of targeting sequence 215 to the complementary sequence in wild-type KRAS sequence 220 results in cleavage (indicated by arrows) of wild-type KRAS sequence 220. Cleavage by Cas9 generates blunt ends 3 nucleotides upstream of the PAM site.

Referring now to FIG. 2B, a mutated KRAS (G12D) allele 225 includes a mutated PAM sequence 5'-TGA-3'. Because the PAM sequence is mutated, Cas9 (not shown) does not bind to mutated KRAS allele 225, targeting sequence 215 is not hybridized, and mutant KRAS allele 225 is not cleaved (i.e., mutated KRAS sequence 225 remains intact).

Cas9 (from *S. pyogenes*) can be used for depletion of a wild-type allele and enrichment of a mutant allele wherein a mutation changes the G residue in a PAM site (5'-NGG-3'). For example, a Cas9 (from *S. pyogenes*) can be used for depletion of a wild-type allele and enrichment of a mutant allele wherein a mutation changes a glycine or proline residue to any other amino acid. Cas9 (from *S. pyogenes*) can also be used for depletion of a wild-type allele and enrichment of a mutant allele wherein a C>T mutation has occurred.

In some embodiments, the Cas9, or variant thereof, is derived from *Streptococcus pyogenes*.

CRISPR systems from other bacterial species (i.e., Cas9 orthologs) that recognize alternative PAM sequences can also be used for depletion of a wild-type allele and enrichment of a mutant allele. For example, Cpfl derived from *Francisell novicida* U112 recognizes a PAM sequence 5'-TTN-3'.

In some embodiments, the first variant of one or more of the plurality of target nucleic acid sequences comprises a PAM site comprising the sequence 5'-TTN-3', wherein N comprises A, G, C, or T, and wherein the second variant does not comprise the PAM site.

In some embodiments, the Cpfl, or variant thereof, is derived from *Francisell novicida* U112.

Figure 3A:
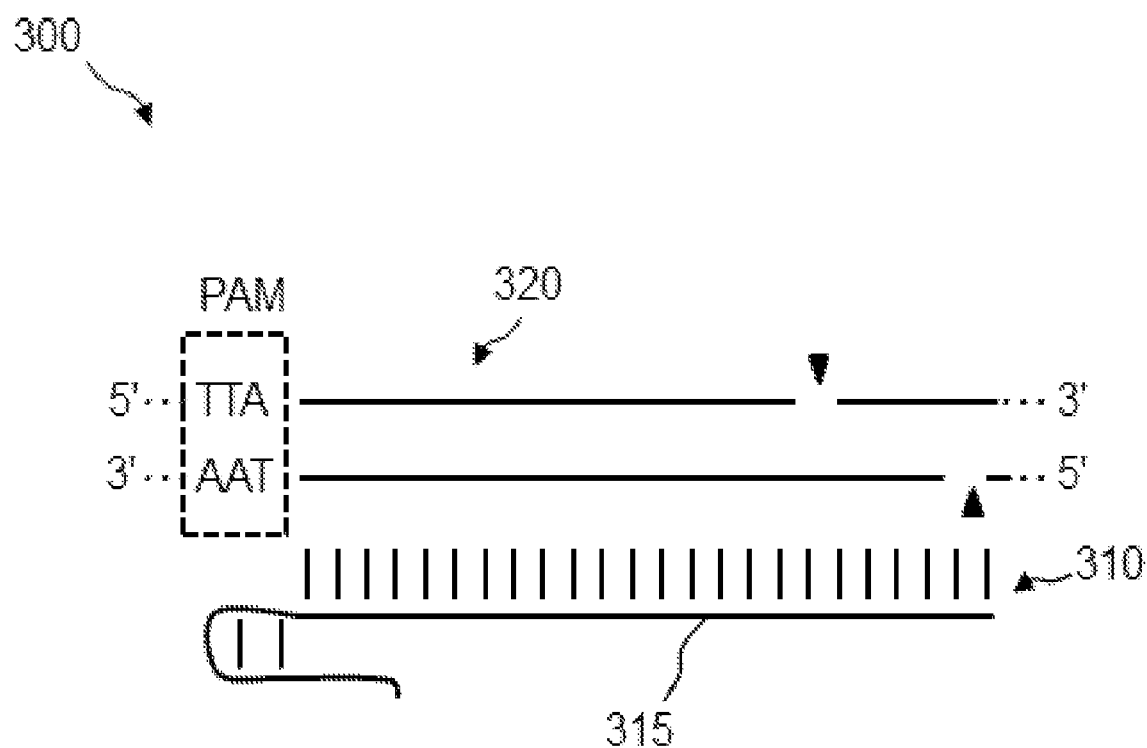
FIGS. 3A and 3B illustrate an example of a process of using Cpfl to selectively deplete a wild-type allele and enrich a mutant DNA allele.
Figure 3B:
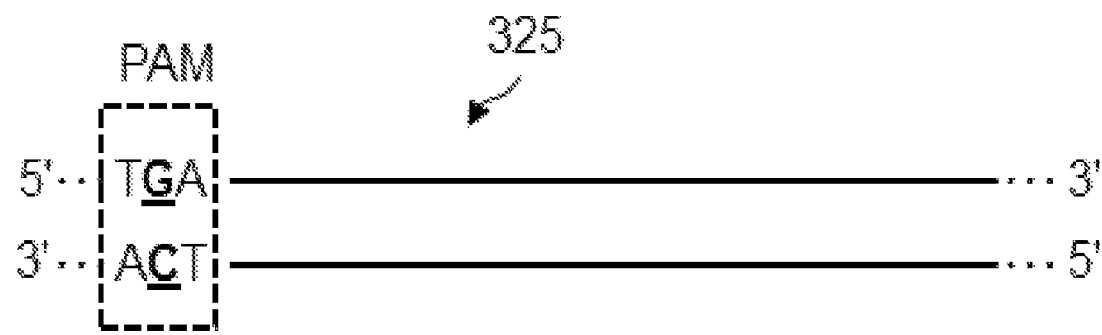

FIGS. 3A and 3B illustrate an example of a process 300 of using Cpfl to selectively deplete a wild-type allele and enrich a mutant DNA allele. In this example, the sequence 5'-TTA-3' is the PAM sequence in a wild-type allele. Referring to FIG. 3A, a guide RNA 310 that includes a 24 base targeting sequence 315 is used in conjunction with Cpfl (not shown) to target a wild-type sequence 320. Targeting sequence 315 is complementary to wild-type sequence 320. Binding of Cpfl (not shown) to the PAM sequence initiates interrogation of the targeted sequences 3' to the PAM site and hybridization of targeting sequence 315 to complementary sequence in wild-type allele 320. Hybridization of targeting sequence 315 to the complementary sequence in wild-type allele 320 results in cleavage (indicated by arrows) of wild-type allele 320. Cpfl cleaves in a staggered fashion, creating a 5 nucleotide 5' overhang 18 to 23 bases away from the PAM site. This approach is applicable for mutations which convert the codons for phenylalanine (UUC and UUU) into any other amino acid expect the U containing codons for leucine (UUA and UUG) and leucine residues encoded by (UUA and UUG) into any other amino acid except phenylalanine.

Referring now to FIG. 3B, a mutated allele 325 includes a mutated Cpfl PAM site 5'-TGA-3'. Because the PAM sequence is mutated, Cpfl (not shown) does not bind to mutated allele 325, targeting sequence 315 is not hybridized, and mutant allele 325 is not cleaved (i.e., mutated allele 325 remains intact). As additional orthologs of Cas9 and Cpfl and their PAM sites are characterized, it will be possible to target additional mutations.

In some embodiments, the first variant of each target nucleic acid comprises a PAM site adjacent to a region complementary to a crRNA targeting sequence, and the second variant does not comprise the region complementary to the crRNA targeting sequence adjacent to the PAM site.

PAM recognition and Cas cleavage can also be used for enrichment and detection of a deletion mutation. For example, a wild-type allele has a PAM site which allows recognition and cleavage by a Cas protein (e.g., Cas9). Deletion of the PAM site in a mutant sequence ablates the PAM site thereby preventing Cas recognition and cleavage.

In some embodiments, the first variant of one or more of the plurality of target nucleic acid sequences comprises a PAM site, and wherein the second variant comprises a deletion of the PAM site.

In some embodiments, the deletion of the PAM site comprises a deletion of 1 or more, 2 or more, 3 or more, 4 or more, 5 or more, 6 or more, 7 or more, 8 or more, 9 or more, 10 or more, 12 or more, 14 or more, 16 or more, 18 or more, 20 or more, 25 or more, 30 or more, 35 or more, 40 or more, 45 or more, or 50 or more base pairs (bps).

In some embodiments, the target nucleic acid comprising a second variant with a PAM deletion mutation comprises EGFR-Exon19del.

In some embodiments, the target nucleic acid comprising a second variant with a PAM deletion mutation comprises a target gene or mutation as shown in FIG. 7.

Figure 4A:
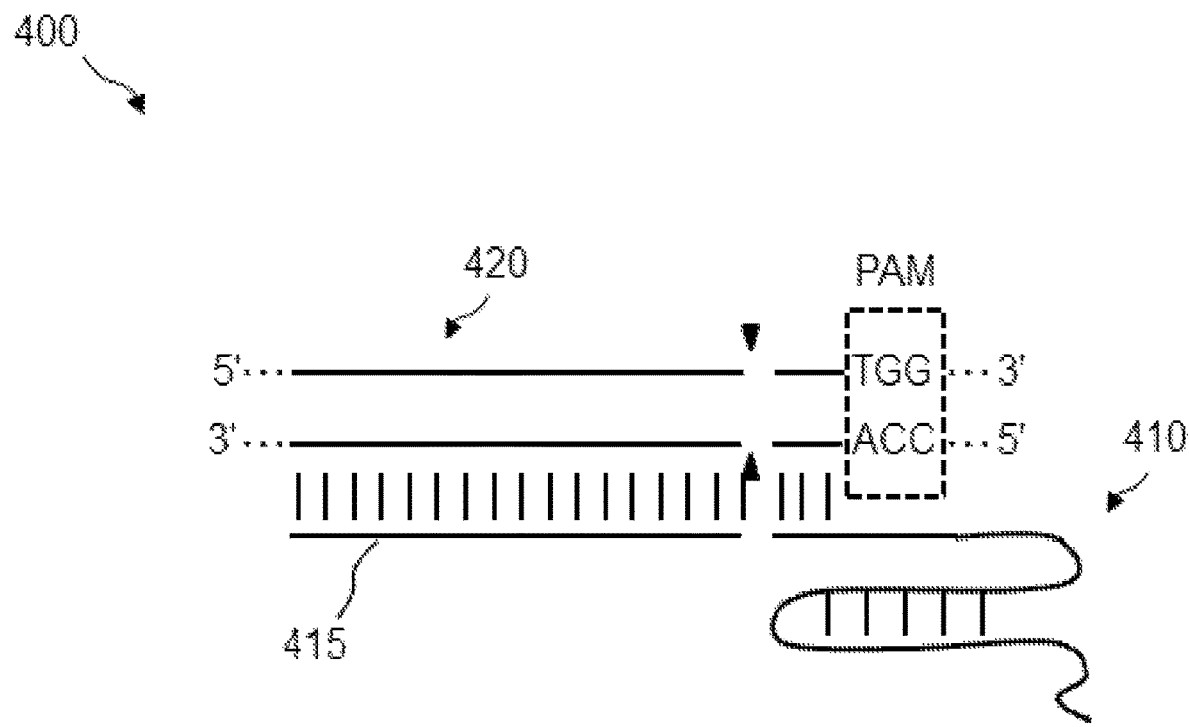
FIGS. 4A and 4B illustrate an example of a process of using Cas9 to selectively deplete a wild-type allele and enrich a DNA sequence that includes a PAM deletion.
Figure 4B:
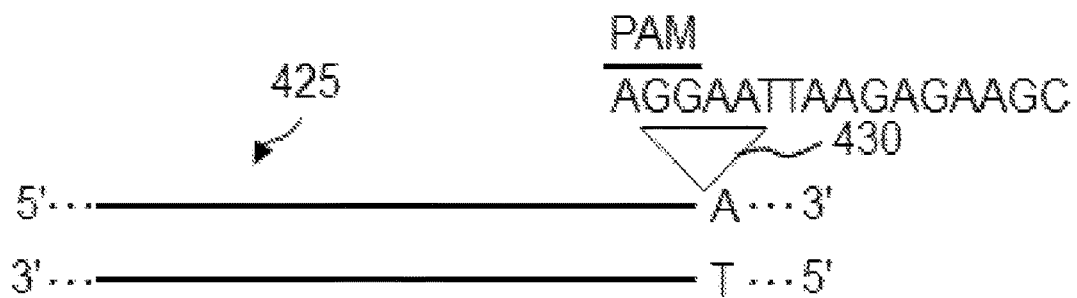

FIGS. 4A and 4B illustrate an example of a process 400 of using Cas9 to selectively deplete a wild-type allele and enrich a DNA sequence that includes a PAM deletion. In this example, the sequence 5'-TGG-3' is the PAM site in a wild-type EGFR allele. Referring to FIG. 4A, a guide RNA 410 that includes a 20 base targeting sequence 415 is used in conjunction with Cas9 (not shown) to target a wild-type EGFR allele 420. Targeting sequence 415 is complementary to wild-type EGFR allele 420. Binding of Cas9 (not shown) to the PAM sequence initiates interrogation of the targeted sequences 5' to the PAM site and hybridization of targeting sequence 415 to complementary sequence in wild-type EGFR allele 420. Hybridization of targeting sequence 415 to the complementary sequence in wild-type EGFR allele 420 results in cleavage (indicated by arrows) of wild-type EGFR allele 420.

Referring now to FIG. 4B, a mutated EGFR (exon 19 del) allele 425 includes a deletion 430 that includes PAM sequence 5'-AGG-3'. Because the PAM site is deleted in the mutant, Cas9 (not shown) does not bind to mutated EGFR sequence 425, targeting sequence 415 is not hybridized, and mutant EGFR allele 425 is not cleaved.

PAM recognition and Cas cleavage can also be used for enrichment and detection of an insertion mutation. For example, an existing PAM site and adjacent target site present in a wild-type allele are separated by an insertion in a mutated sequence. Because the PAM site is separated from the target site, Cas recognition and cleavage of the mutant sequence does not occur.

In some embodiments, the first variant of one or more of the plurality of target nucleic acid sequences comprises a region complementary to a crRNA targeting sequence adjacent to a PAM site and the second variant comprises an insertion of 1 or more, 2 or more, 3 or more, 4 or more, 5 or more, 6 or more, 7 or more, 8 or more, 9 or more, 10 or more, 12 or more, 14 or more, 16 or more, 18 or more, or 20 or more base pairs (bps) within 50 bps, 40 bps, 30 bps, 20 bps, or 10 bps upstream (on the 5'-end) of the PAM site.

Figure 5A:
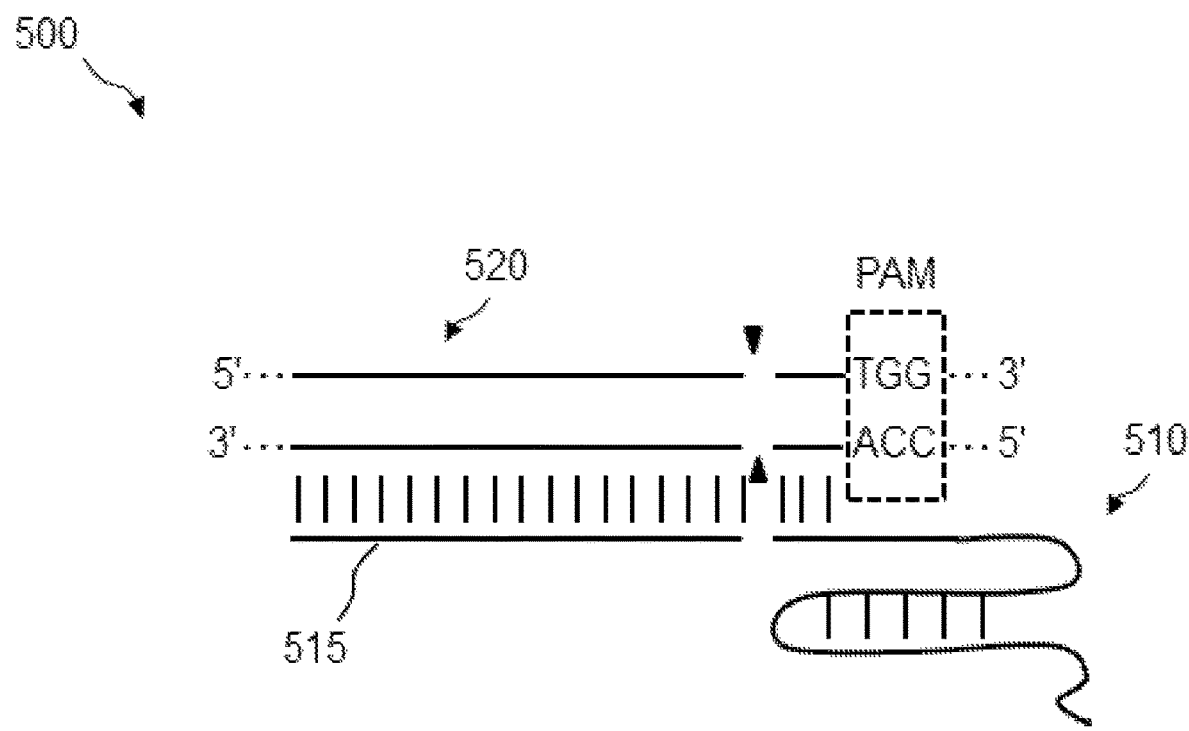
FIGS. 5A and 5B illustrate an example of a process of using Cas9 to selectively deplete a wild-type allele and enrich a mutant allele that includes an insertion mutation.
Figure 5B:
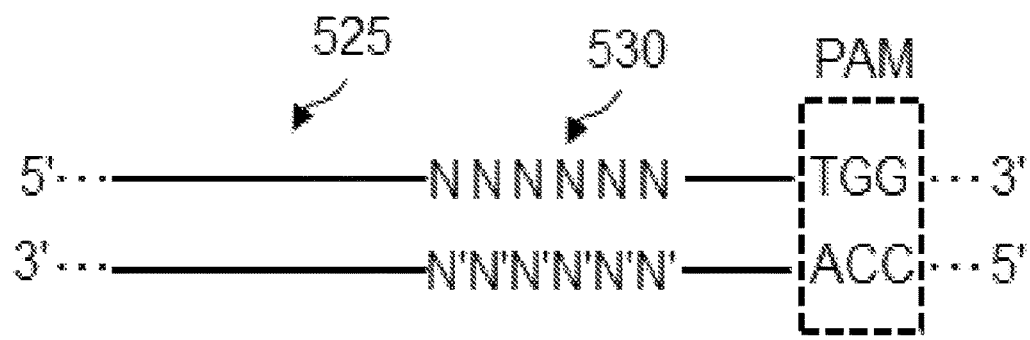

FIGS. 5A and 5B illustrate an example of a process 500 of using Cas9 to selectively deplete a wild-type allele and enrich a mutant allele that includes an insertion mutation. In this example, the sequence 5'-TGG-3' is the PAM sequence in a wild-type allele. Referring to FIG. 5A, a guide RNA 510 that includes a 20 base targeting sequence 515 is used in conjunction with Cas9 (not shown) to target a wild-type sequence 520. Targeting sequence 515 is complementary to wild-type allele 520. Binding of Cas9 (not shown) to the PAM sequence initiates interrogation of the targeted sequences 5' to the PAM site and hybridization of targeting sequence 515 to the complementary sequence in wild-type allele 520. Hybridization of targeting sequence 515 to the complementary sequence in wild-type allele 520 results in cleavage (indicated by arrows) of wild-type allele 520.

Referring now to FIG. 5B, a mutated allele 525 includes an insertion 530 that interrupts the sequence targeted by targeting sequence 515, i.e., wild-type sequence 520. Because mutated allele 525 includes insertion 530 that interrupts the wild-type sequence 520, complete or near complete hybridization of targeting region 515 to mutated sequence 525 does not occur and mutated allele 525 is not cleaved.

Single Base Specificity for Differential Cleavage and Enrichment of Mutations in ctDNA In some embodiments, the first variant of each target nucleic acid comprises a PAM site adjacent to a region complementary to a crRNA targeting sequence, and the second variant comprises the PAM site and does not comprise the region complementary to the crRNA targeting sequence.

In some embodiments, the region in the second variant corresponding to the crRNA targeting sequence in the first variant comprises a point mutation (e.g., 1 bp, 2 bps, or 3 bps point mutation). In some embodiments, the region in the second variant corresponding to the crRNA targeting sequence comprises a deletion mutation (e.g., deletion of 1 bp, 2 bps, 3 bps, 4 bps, 5 bps, 6 bps, 7 bps, 8 bps, 9 bps, 10 bps, or more). In some embodiments, the region in the second variant corresponding to the crRNA targeting sequence comprises an insertion mutation (e.g., deletion of 1 bp, 2 bps, 3 bps, 4 bps, 5 bps, 6 bps, 7 bps, 8 bps, 9 bps, 10 bps, or more).

In some embodiments, the target nucleic acid comprising a mutation in the crRNA targeting sequence comprises BRAF (e.g., BRAF-V600E, BRAF-L597V), EGFR (e.g., EGFR-T790M, E709 T710delins), KRAS (e.g., KRAS-Q61H, KRAS-Q61L, KRAS-Q61R, KRAS-Q61K), MAP2K1 (e.g., MAP2K1-Q56P), NRAS (e.g., NRAS-Q61H, NRAS-Q61L, NRAS-Q61R, NRAS-Q61K), PIK3CA (e.g., PIK3CA-E542K, PIK3CA-E545Q, PIK3CA-E545K, PIK3CA-H1047R, PIK3CA-H104L), or PTEN (e.g., PTEN-R233*(Stop Codon)).

In some embodiments, the mutation in the crRNA targeting sequence comprises a A>C, A>G, A>T, C>A, C>G, C>T, G>A, G>C, G>T, T>A, T>C, or T>G mutation.

In some embodiments, the target nucleic acid comprising a mutation in a crRNA targeting sequence comprises a target gene or mutation as shown in FIG. 7.

Cas cleavage of a targeted DNA sequence occurs if there is sufficient complementarity between the guide RNA (crRNA) targeting sequence and the targeted DNA. The targeting sequence of a guide RNA can be designed to discriminate between a wild-type allele and a mutant allele (s), wherein the mutant allele includes a mutation in the region targeted by the guide RNA.

In one example, addition of one or more base mismatches in the targeting region of a guide RNA can be used to enhance the specificity of a guide RNA and discriminate between a wild-type allele and a mutant allele(s).

In another example, truncation of the targeting region of a guide RNA can be used to enhance the specificity of a guide RNA and discriminate between a wild-type allele and a mutant allele(s).

Figure 6A:
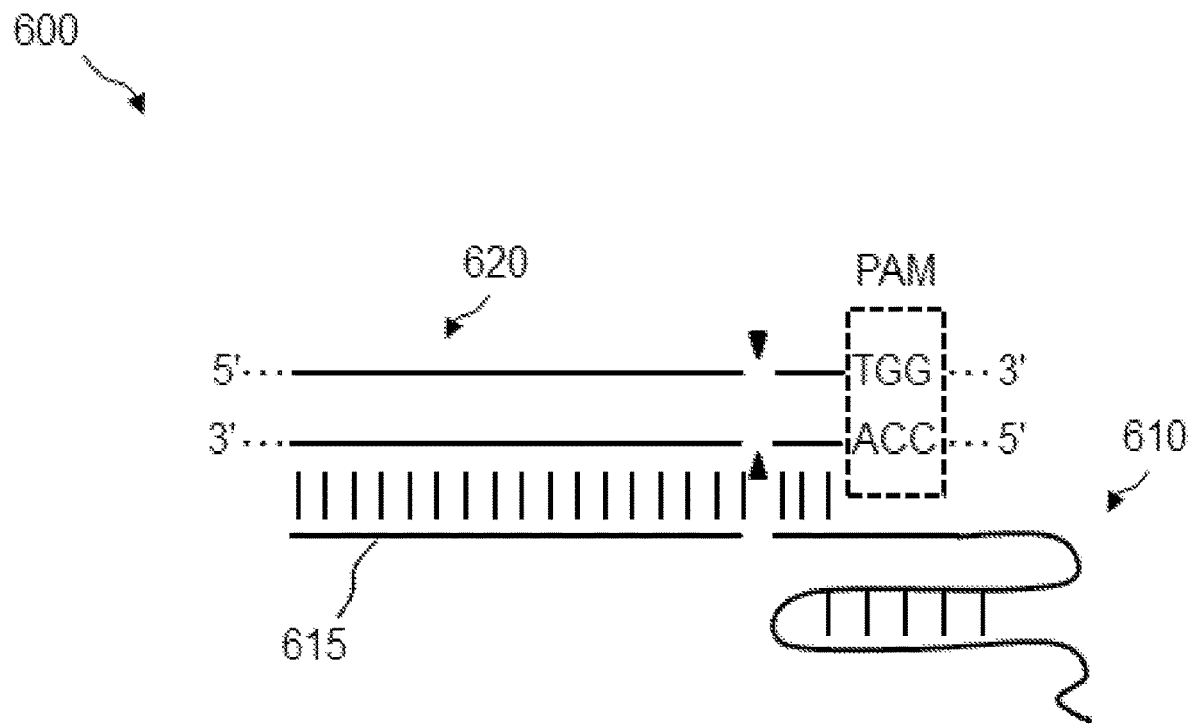
FIGS. 6A and 6B illustrate an example of a process of using Cas9 to selectively deplete a wild-type BRAF allele and enrich a mutant allele that includes a single base mutation in the region targeted by a guide RNA.
Figure 6B:
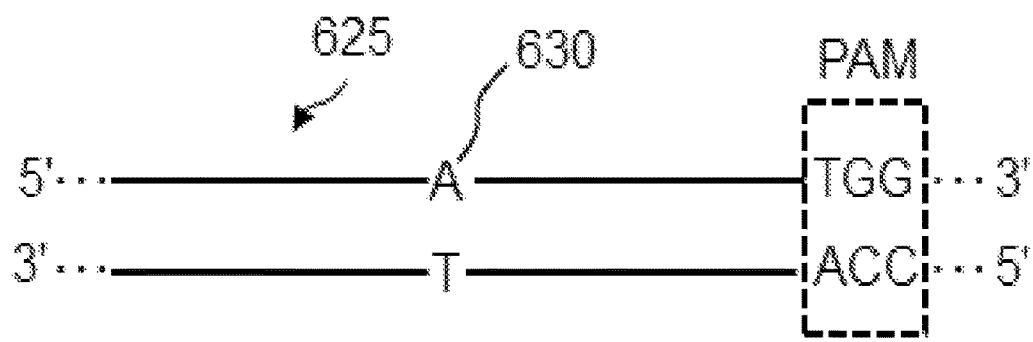

FIGS. 6A and 6B illustrate an example of a process 600 of using Cas9 to selectively deplete a wild-type BRAF allele and enrich the mutant V600E mutant allele that includes a single base mutation in the region targeted by a guide RNA. Referring to FIG. 6A, a guide RNA 610 that includes a 20 base targeting sequence 615 is used in conjunction with Cas9 (not shown) to target a wild-type BRAF allele 620. Targeting sequence 615 is complementary to wild-type BRAF allele 620. Binding of Cas9 (not shown) to the PAM site initiates interrogation of the targeted sequences 5' to the PAM site and hybridization of targeting sequence 615 to the complementary sequence in wild-type BRAF allele 620. Hybridization of targeting sequence 615 to the complementary sequence in wild-type BRAF allele 620 results in cleavage (indicated by arrows) of wild-type BRAF allele 620.

Referring now to FIG. 6B, a mutant BRAF V600E allele 625 includes a single base mutation 630 that changes a wild-type T residue to an A residue. Mutation 630 disrupts the complementarity between targeting sequence 615 and mutant BRAF V600E allele 625 is not cleaved.

Cas9 Enrichment Panel for Cancer Detection and Diagnosis

In some embodiments, provided herein is a "tool box" of Cas proteins that are programmed with a set of guide RNAs having different wild-type specificities. The tool box of Cas proteins constitutes an "enzymatic enrichment panel" that can be used for multiplexed enrichment of multiple mutated sequences. The tool box can include, for example, Cas proteins (i.e., Cas9 and Cas9 orthologs) with different PAM site recognition (e.g., Cas9: 5'-NGG-3; Cpf1: 5'-TTN-3') and guide RNAs having targeting sequences with enhanced single base specificity for discriminating between a wild-type allele and a mutant allele. In one example, the enzymatic enrichment panel can be used alone for enrichment of mutant alleles for cancer detection and diagnosis. In another example, the enzymatic enrichment panel can be used in combination with an oligonucleotide probe-based enrichment system.

FIG. 7 shows a table 700 of an example of a screening strategy for hotspot mutations in non-small cell lung cancer (NSCLC). Shown in table 700 are targeted genes (Gene-Name), the reference base (REF), the mutated base (ALT), the resulting mutation (Mutation), and targeting strategy for depleting the wild-type allele (Strategy) for each hotspot region. For example (A), in the BRAF gene, the V600E mutation results in an amino acid substitution at position 600 (from a valine (V) to a glutamic acid (E)), wherein an A to T single base change in the region targeted by the targeting sequence of a Cas9 guide RNA. Because of the single base change, a guide RNA with single base specificity can be used to target the wild-type BRAF allele for cleavage as described above with reference to FIGS. 6A and 6B.

In another example (B), in the EGFR gene, a deletion in exon 19 (Exon19del) ablates a Cas9 PAM site in a mutant allele. Because the Cas9 PAM site is disrupted in the mutant allele, Cas9 and a guide RNA with a targeting sequence complementary to the sequence adjacent to the PAM site can be used to target the wild-type EGFR allele for cleavage as described above with reference to FIGS. 4A and 4B.

In yet another example (C), in the KRAS gene, the G12D mutation results in an amino acid substitution at position 12 (from a glycine (G) to an aspartic acid (D)), wherein a G to A base change ablates a Cas9 PAM site. Because the Cas9 PAM site is disrupted in the mutant allele, Cas9 and a guide RNA with a targeting sequence complementary to the sequence adjacent to the PAM site can be used to target the wild-type KRAS allele for selective cleavage as described above with reference to FIGS. 2A and 2B.

In some embodiments, the mutant allele sequence comprises a AKT1-E17K, BRAF-V600E, BRAF-L597V, BRAF-G469A, BRAF-G466V, EGFR-E709 T710delins, EGFR-G719S, EGFR-G719C, EGFR-G719A, EGFR-Exon19del, EGFR-T790M, EGFR-L858R, EGFR-L861Q, KRAS-Q61H, KRAS-Q61L, KRAS-Q61R, KRAS-Q61K, KRAS-G13A, KRAS-G13D, KRAS-G13C, KRAS-G13R, KRAS-G13D, KRAS-G13C, KRAS-G13R, KRAS-G13S, KRAS-G12V, KRAS-G12A, KRAS-G12D, KRAS-G12D, KRAS-G12C, KRAS-G12R, KRAS-G12S, MAP2K1-Q56P, NRAS-Q61H, NRAS-Q61L, NRAS-Q61R, NRAS-Q61K, NRAS-G12A, NRAS-G12D, NRAS-G12C, NRAS-G12R, NRAS-G12S, PI3KCA-E542K, PI3KCA-E545Q, PI3KCA-E545K, PI3KCA-H1047R, PI3KCA-H1047L, or PTEN-R233* mutant allele sequence.

In some embodiments, the mutant allele sequence comprises a mutant allele sequence according to FIG. 7.

Analysis of Cell Free RNA

Abundant transcripts can overwhelm detection of less abundant transcripts during analysis of an RNA-Seq library prepared from cell free RNA isolated from a biological sample. In some embodiments, the methods provided herein are used to deplete unwanted high-abundance sequences from an RNA-Seq library. Examples of unwanted high-abundance sequences include, but are not limited to, ribosomal RNA and globin RNA.

In some embodiments, the methods provided herein are used to enrich for a fusion transcript (RNA fusions). A fusion transcript is a chimeric RNA encoded, for example, by a fusion gene created by DNA translocation between two genes in their introns and subsequent splicing to remove the intron, or by the trans-splicing of exons in two different transcripts. Certain fusion transcripts are commonly produced by cancer cells, and detection of fusion transcripts is part of routine diagnostics of certain cancer types (e.g Temprss2-Erg translocations in prostate cancer).

In some embodiments, the endonuclease system further comprises a crRNA and Cas protein targeting an abundant wild-type target nucleic acid in the sample. In some embodiments, the abundant wild-type target nucleic acid is a ribonucleic acid (e.g., a rRNA, mRNA (e.g., a globin mRNA), or tRNA). In some embodiments, the abundant wild-type target nucleic acid is selected from the group consisting of a ribosomal RNA and a globin RNA.

In some embodiments, in the second variant the region adjacent to the PAM site comprises the junction of a fusion gene.

Figure 8A:
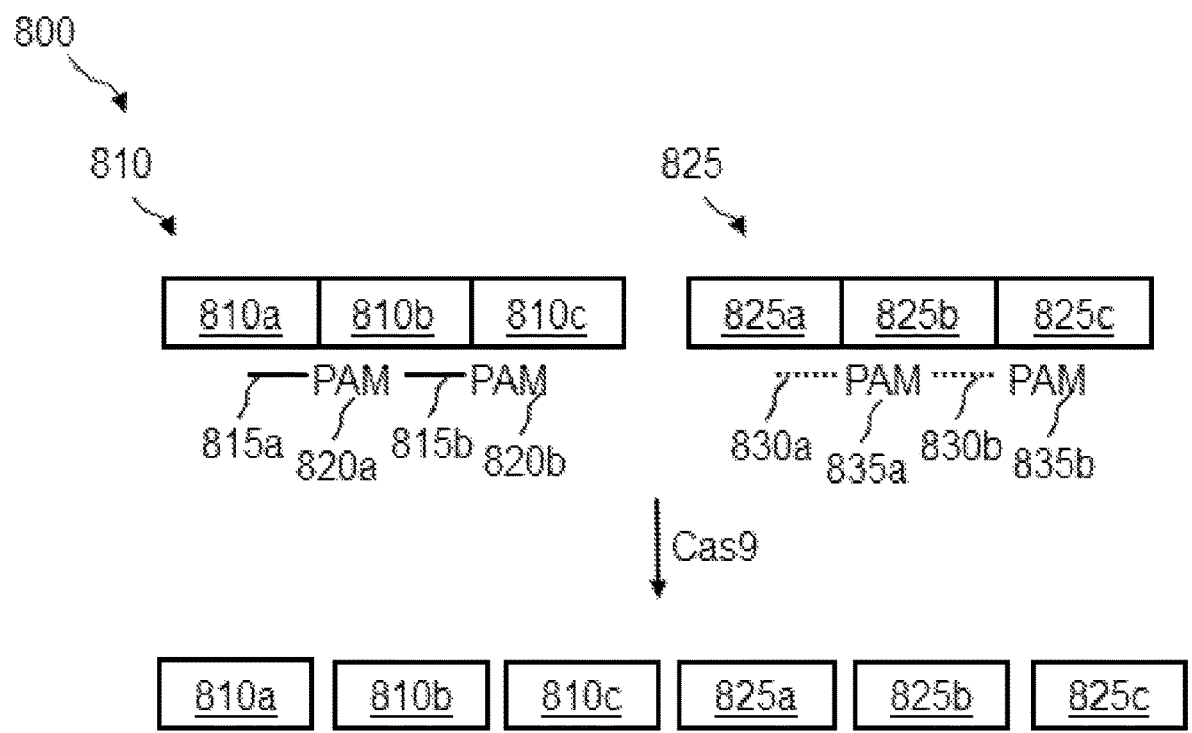
FIGS. 8A and 8B illustrate an example of a process of using Cas9 to detect a fusion event in a RNA-Seq library prepared from cell free RNA isolated from a biological sample.
Figure 8B:
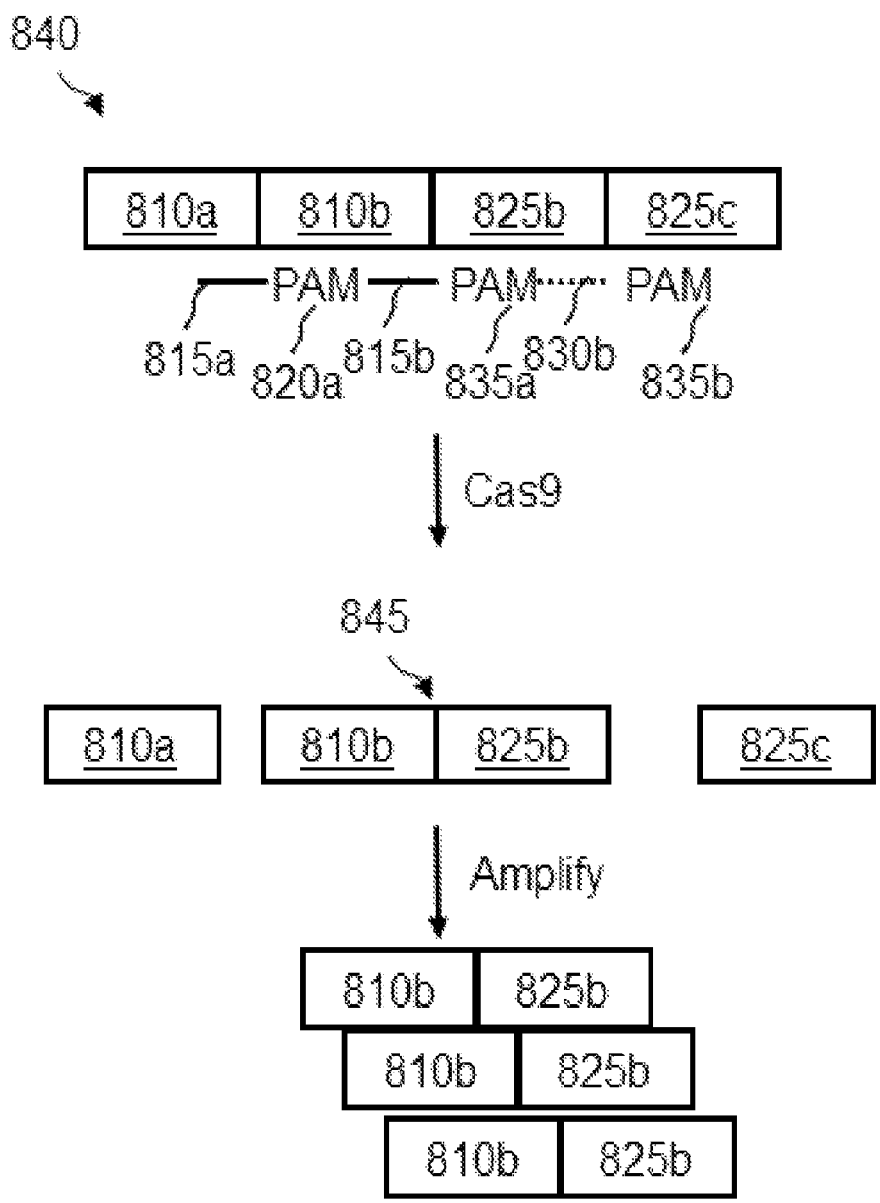

FIGS. 8A and 8B illustrate an example of a process 800 of using Cas9 to detect an RNA fusion event. Referring to FIG. 8A, first transcript cDNA 810 includes sequences from three exons (i.e., 810a, 810b, and 810c) from a first gene, wherein each junction between exon sequences is characterized by a targeting sequence 815 (i.e., 815a and 815b) on the 5'-end and a first PAM site 820 (i.e., 820a and 820b) on the 3'-end. A second transcript cDNA 825 includes sequences from three exons (i.e., 825a, 825b, and 825c) from a second gene, wherein each junction between exon sequences is characterized by a targeting sequence 830 (i.e., 830a and 830b) on the 5'-end and a second PAM site 835 (i.e., 835a and 835b) on the 3'-end. First PAM site 820 and second PAM site 835 are recognized by different Cas9 proteins. Binding of Cas9 complexes (not shown) to the PAM sites initiates interrogation of the targeted sequences 5' to the PAM site and sufficient hybridization of targeting sequences 815 and 830 to their complementary target sequences results in cleavage of the targeted sequences.

Referring to FIG. 8B, a fusion transcript cDNA 840 includes sequences from transcript 810 (i.e., 810a and 810b) and transcript 825 (i.e., 825b and 825c). The fusion event creates a new junction 845 between exon sequences 810b and 825b, and separates PAM site 825b from its neighboring targeting site 830a, thereby preventing cleavage at junction 845.

Genome Wide Applications of Cas Cleavage to Diagnose Changes in Cancer Genomes

CRISPR-Cas systems can be used to mediate differential nucleic acid fragmentation for preparation of a genomic library for sequencing. For example, a pool of Cas9 proteins that are programmed with guide RNAs targeting regions across a genome (e.g., a reference genome) can be used for targeted fragmentation of genomic DNA for subsequent sequencing.

In another aspect, provided herein is a method for analyzing the genome of a cancer patient, comprising providing an endonuclease system, wherein the endonuclease system comprises a plurality of crRNAs, or derivatives thereof, each crRNA comprising a targeting sequence, and a plurality of Cas proteins, or variants thereof, each Cas protein capable of binding to a PAM site on a target nucleic acid; contacting a sample obtained from the cancer patient comprising a plurality of target nucleic acids with the endonuclease system to obtain a pool of target nucleic acid fragments; sequencing the pool of target nucleic acid fragments to obtain sequencing data from the cancer patient, and comparing the sequencing data from the cancer patient with sequencing data from a reference genome fragmented by the endonuclease system to detect structural rearrangements and mutations in the genome of the cancer patient.

In some embodiments, the sequencing data comprises comparing the fragmentation pattern of the pool of target nucleic acids from the cancer patient with the fragmentation pattern of a pool of target nucleic acids in the reference genome.

In some embodiments, the method comprises contacting a sample obtained from a healthy subject comprising a plurality of target nucleic acids with the endonuclease system to obtain a pool of target nucleic acid fragments, and sequencing the pool of target nucleic acid fragments to obtain the sequencing data from the reference genome.

In some embodiments, the endonuclease system cleaves target nucleic acids in a sample from a healthy subject at a predetermined interval.

In some embodiments, the predetermined interval is about 300 bp.

Figure 9:
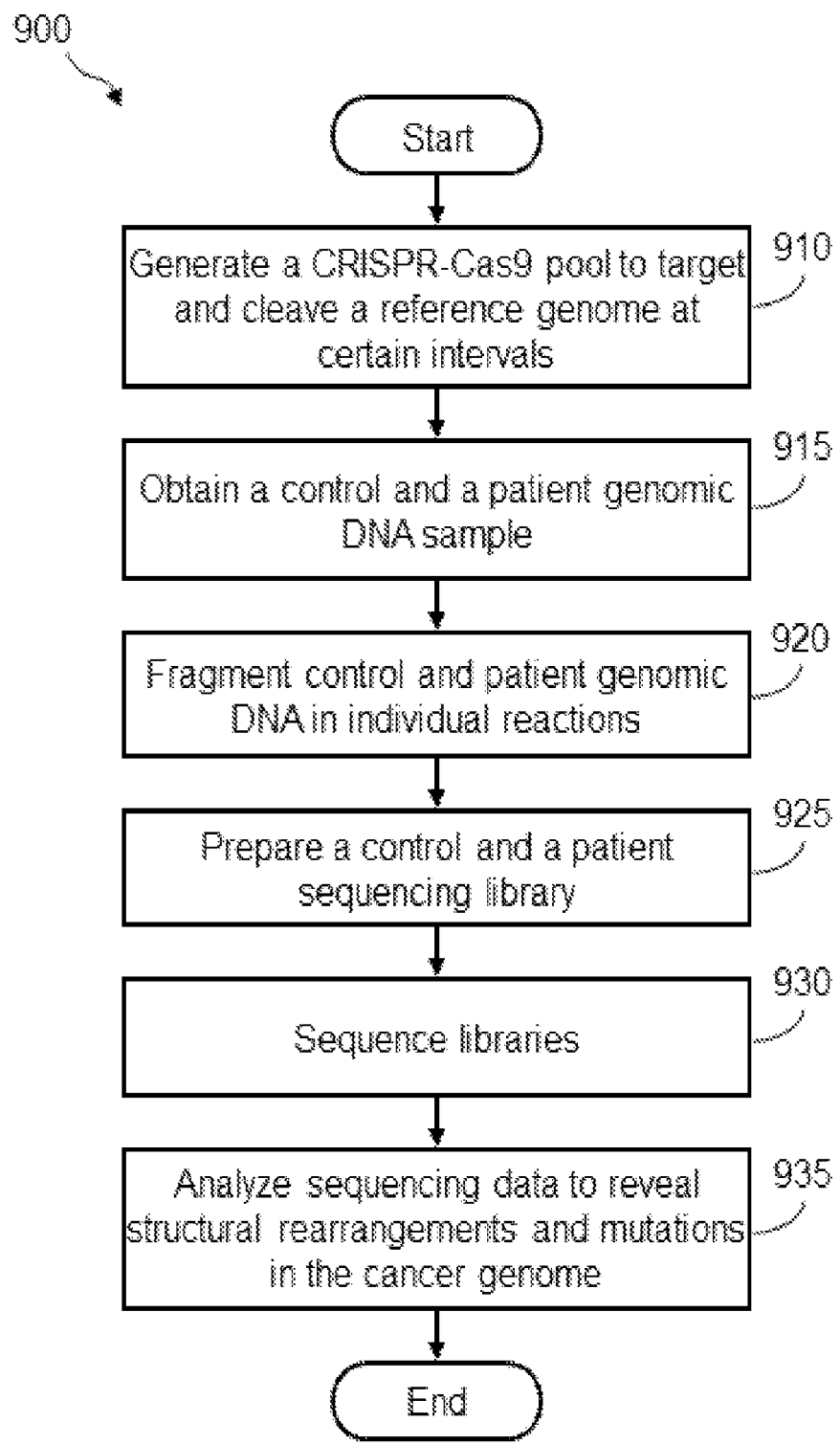
FIG. 9 illustrates a flow diagram of an example of a method of using targeted Cas9 cleavage to characterize a cancer genome.

FIG. 9 illustrates a flow diagram of an example of a method 900 of using targeted Cas9 cleavage to characterize a cancer genome. In this example, sequencing libraries are prepared using genomic DNA from a healthy subject and genomic DNA from a cancer patient. Method 900 includes, but is not limited to, the following steps.

In a step 910, a pool of Cas9 proteins that are programmed with guide RNAS targeting regions across a reference genome is prepared. In one example, the pool of Cas9 proteins is prepared such that genomic DNA is cleaved about every 300 bp.

In a step 915, genomic DNA samples from a healthy control subject and a cancer patient are obtained.

In a step 920, genomic DNA from the control subject and the cancer patient are fragmented (in separate reactions) using the pool of Cas9 proteins.

In a step 925, sequencing libraries are prepared from the fragmented control DNA and the patient DNA.

In a step 930, the libraries are sequenced.

In a step 935, the sequencing data is analyzed to reveal structural rearrangements and mutations in the cancer genome.

Sample Types and Disease Conditions

Methods in accordance with embodiments of the invention can be carried out on any suitable sample type that contains a plurality of nucleic acids, as described above. For example, in some embodiments, a sample comprises a biological fluid. Non-limiting examples of biological fluids include, e.g., blood, plasma, serum, urine, saliva, pleural fluid, pericardial fluid, cerebrospinal fluid (CSF), peritoneal fluid, amniotic fluid, and combinations thereof. In some embodiments, a sample comprises a non-liquid biological sample. Non-limiting examples of non-liquid biological samples include tissue biopsies, such as, e.g., a cancerous tissue biopsy, a healthy tissue biopsy, a fetal tissue sample, or a combination thereof. In some embodiments, a sample comprises a liquid or a non-liquid biological sample collected from a transplanted organ.

In some embodiments, the subject methods are carried out on a patient having or suspected of having a cancer. In some embodiments, a patient is a human or non-human animal. Non-limiting examples of cancers include, e.g., a carcinoma, a sarcoma, a myeloma, a leukemia, a lymphoma, a blastoma, a germ cell tumor, or any combination thereof. In some embodiments, a carcinoma is an adenocarcinoma. In some embodiments, a carcinoma is a squamous cell carcinoma. In some embodiments, a carcinoma is a small cell lung cancer, non-small-cell lung, nasopharyngeal, colorectal, anal, liver, urinary bladder, testicular, cervical, ovarian, gastric, esophageal, head-and-neck, pancreatic, prostate, renal, thyroid, melanoma, or breast carcinoma. In some embodiments, a breast cancer is hormone receptor negative breast cancer or triple negative breast cancer.

In some embodiments, a sarcoma is an osteosarcoma, chondrasarcoma, leiomyosarcoma, rhabdomyosarcoma, mesothelial sarcoma (mesothelioma), fibrosarcoma, angiosarcoma, liposarcoma, glioma, or astrocytoma.

In some embodiments, a leukemia is a myelogenous, granulocytic, lymphatic, lymphocytic, or lymphoblastic leukemia. In some embodiments, a lymphoma is selected from the group consisting of: Hodgkin's lymphoma and Non-Hodgkin's lymphoma.

In some embodiments, the subject methods are carried out on a sample that is obtained from a pregnant female patient. In some embodiments, a sample is obtained from a fetus that is gestating within a pregnant female patient. In some embodiments, a pregnant female patient is a human.

In some embodiments, the subject methods are carried out on a sample that is obtained from a patient that has undergone an organ transplantation procedure, and the sample is obtained from the patient, or is obtained directly from the transplanted organ.

In some embodiments, the subject methods are carried out on a sample that is obtained from a healthy patient, or from a patient with a known disease condition (e.g., a previously diagnosed cancer).

The methods of the present disclosure find use in connection with any of a variety of healthy and/or disease conditions. For example, in some embodiments, the subject methods are carried out on a sample that is obtained from a healthy subject. In some embodiments, the subject methods are carried out on a sample that is obtained from a subject that is suspected of having an unknown disease or condition, e.g., an unknown cancer, or an unknown genetic abnormality. In some embodiments, the subject methods are carried out on a sample that is obtained from a subject that is known to have a specific disease or condition, e.g., a specific type of cancer.

In some embodiments, the subject methods are carried out on a sample from a pregnant female patient, and the methods involve analyzing a sample that is obtained from the pregnant female patient, from a gestating fetus within the pregnant female patient, or both.

In some embodiments, the subject methods are carried out on a sample from a patient that has undergone an organ transplantation procedure, and the methods involve analyzing a sample that is obtained from the patient, from the transplanted organ, or both.

CONCLUDING REMARKS

The foregoing detailed description of embodiments refers to the accompanying drawings, which illustrate specific embodiments of the present disclosure. Other embodiments having different structures and operations do not depart from the scope of the present disclosure. This specification is divided into sections for the convenience of the reader only. Headings should not be construed as limiting of the scope of the methods or compositions provided herein. The definitions are intended as a part of the description of the methods or compositions provided herein. It will be understood that various details of the methods or compositions provided herein can be changed without departing from the scope of the methods or compositions provided herein. Furthermore, the foregoing description is for the purpose of illustration only, and not for the purpose of limitation.

What is claimed is:

1. A method for enriching a plurality of target nucleic acids in a sample, the method comprising:
providing an endonuclease system;
wherein each of the plurality of target nucleic acids comprises:
a first variant comprising a wild-type allele sequence selected from the group consisting of: AKT1, BRAF, EGFR, KRAS, MAP2K1, NRAS, PI3KCA and PTEN; and
a second variant,
wherein the endonuclease system comprises a plurality of clustered regularly interspaced short palindromic repeat (CRISPR) RNAs (crRNAs), or derivatives thereof, each crRNA comprising a targeting sequence, and a plurality of CRISPR-associated (Cas) proteins, or variants thereof, each Cas protein capable of binding to a protospacer adjacent motif (PAM) site on a target nucleic acid,
wherein the first variant of each target nucleic acid comprises a PAM site adjacent to a region complementary to a crRNA targeting sequence, and wherein the second variant does not comprise the PAM site or does not comprise the region complementary to the crRNA targeting sequence adjacent to the PAM site, and
contacting the sample with the endonuclease system, thereby depleting the first variant and enriching the second variant of each of the plurality of target nucleic acids in the sample.

2. The method of claim 1, wherein the second variant of each of the plurality of target nucleic acids comprises a mutant allele sequence.

3. The method of claim 2, wherein the mutant allele sequence comprises a mutant allele sequence selected from the group consisting of: AKT1, BRAF, EGFR, KRAS, MAP2K1, NRAS, PI3KCA and PTEN.

4. The method of claim 2, wherein the mutant allele sequence is selected from the group consisting of: AKT1-E17K, BRAF-V600E, BRAF-L597V, BRAF-G469A, BRAF-G466V, EGFR-E709_T710delins, EGFR-G719S, EGFR-G719C, EGFR-G719A, EGFR-Exon19del, EGFR-T790M, EGFR-L858R, EGFR-L861Q, KRAS-Q61H, KRAS-Q61L, KRAS-Q61R, KRAS-Q61K, KRAS-G13A, KRAS-G13D, KRAS-G13C, KRAS-G13R, KRAS-G13D, KRAS-G13C, KRAS-G13R, KRAS-G13S, KRAS-G12V, KRAS-G12A, KRAS-G12D, KRAS-G12D, KRAS-G12C, KRAS-G12R, KRAS-G12S, MAP2K1-Q56P, NRAS-Q61H, NRAS-Q61L, NRAS-Q61R, NRAS-Q61K, NRAS-G12A, NRAS-G12D, NRAS-G12C, NRAS-G12R, NRAS-G12S, PI3KCA-E542K, PI3KCA-E545Q, PI3KCA-E545K, PI3KCA-H1047R, PI3KCA-H1047L, and PTEN-R233*.

5. The method of claim 2, wherein the mutant allele sequence comprises a mutant allele sequence according to FIG. 7.

6. The method of claim 1, wherein the sample comprises a blood, serum, plasma, urine, or cerebrospinal fluid sample.

7. The method of claim 1, wherein the plurality of target nucleic acids comprises cell-free DNA (cfDNA) or cell-free RNA (cfRNA).

8. The method of claim 1, wherein the plurality of Cas proteins comprises Cas9, or a variant thereof, a Cas9 ortholog, or a variant thereof, or Cpf1, or a variant thereof, and wherein the Cas9, or variant thereof, is derived from *Streptococcus pyogenes*, or wherein the Cpf1, or variant thereof, is derived from *Francisell novicida* U112.

9. The method of claim 1, wherein the first variant of each target nucleic acid comprises a PAM site adjacent to a region complementary to a crRNA targeting sequence, and the second variant does not comprise the PAM site.

10. The method of claim 1, wherein the first variant of each target nucleic acid comprises a PAM site adjacent to a region complementary to a crRNA targeting sequence, and the second variant does not comprise the region complementary to the crRNA targeting sequence adjacent to the PAM site.

11. The method of claim 1, wherein the first variant of one or more of the plurality of target nucleic acid sequences comprises a PAM site comprising the sequence 5'-TTN-3', wherein N comprises A, G, C, or T, and wherein the second variant does not comprise the PAM site.

12. The method of claim 1, wherein the first variant of one or more of the plurality of target nucleic acid sequences comprises a PAM site, and wherein the second variant comprises a deletion of the PAM site.

13. The method of claim 1, wherein the first variant of one or more of the plurality of target nucleic acid sequences comprises a region complementary to a crRNA targeting sequence adjacent to a PAM site and the second variant comprises an insertion of 1 or more, 2 or more, 3 or more, 4 or more, 5 or more, 6 or more, 7 or more, 8 or more, 9 or more, 10 or more, 12 or more, 14 or more, 16 or more, 18 or more, or 20 or more base pairs (bps) within 50 bps, 40 bps, 30 bps, 20 bps, or 10 bps upstream of the PAM site.

14. The method of claim 1, wherein the first variant of one or more of the plurality of target nucleic acid sequences comprises a region complementary to a crRNA targeting sequence adjacent to a PAM site, and the second variant does not comprise the region complementary to the crRNA targeting sequence adjacent to the PAM site.

15. The method of claim 14, wherein in the second variant the region adjacent to the PAM site comprises a point mutation.

16. The method of claim 14, wherein in the second variant the region adjacent to the PAM site comprises the junction of a fusion gene.

17. The method of claim 1, wherein the endonuclease system further comprises a crRNA and Cas protein targeting an abundant wild-type target nucleic acid in the sample.

18. The method of claim 17, wherein the abundant wild-type target nucleic acid is selected from the group consisting of a ribosomal RNA and a globin RNA.

19. A method for enriching a plurality of target nucleic acids in a sample, the method comprising:
providing an endonuclease system;
wherein each of the plurality of target nucleic acids comprises a first variant and a second variant,
wherein the endonuclease system comprises a plurality of clustered regularly interspaced short palindromic repeat (CRISPR) RNAs (crRNAs), or derivatives thereof, each crRNA comprising a targeting sequence, and a plurality of CRISPR-associated (Cas) proteins, or variants thereof, each Cas protein capable of binding to a protospacer adjacent motif (PAM) site on a target nucleic acid,
wherein the first variant of each target nucleic acid comprises a PAM site adjacent to a region complementary to a crRNA targeting sequence adjacent to the PAM site, and wherein the second variant does not comprise the region complementary to the crRNA targeting sequence adjacent to the PAM site, and wherein in the second variant the region adjacent to the PAM site comprises the junction of a fusion gene; and contacting the sample with the endonuclease system, thereby depleting the first variant and enriching the second variant of each of the plurality of target nucleic acids in the sample.

20. The method of claim 19, wherein in the second variant the region adjacent to the PAM site comprises a point mutation.

21. A method for enriching a plurality of target nucleic acids in a sample, the method comprising:

providing an endonuclease system;

wherein each of the plurality of target nucleic acids comprises a first variant and a second variant, wherein the endonuclease system comprises a plurality of clustered regularly interspaced short palindromic repeat (CRISPR) RNAs (crRNAs), or derivatives thereof, each crRNA comprising a targeting sequence, and a plurality of CRISPR-associated (Cas) proteins, or variants thereof, each Cas protein capable of binding to a protospacer adjacent motif (PAM) site on a target nucleic acid, wherein the endonuclease system further comprises a crRNA and Cas protein targeting an abundant wild-type target nucleic acid in the sample, wherein the abundant wild-type target nucleic acid is selected from the group consisting of: a ribosomal RNA and a globin RNA;

wherein the first variant of each target nucleic acid comprises a PAM site adjacent to a region complementary to a crRNA targeting sequence, and wherein the second variant does not comprise the PAM site or does not comprise the region complementary to the crRNA targeting sequence adjacent to the PAM site, and contacting the sample with the endonuclease system, thereby depleting the first variant and enriching the second variant of each of the plurality of target nucleic acids in the sample.

\* \* \* \* \*